US009365659B2

(12) United States Patent
Youngbull et al.

(10) Patent No.: US 9,365,659 B2
(45) Date of Patent: Jun. 14, 2016

(54) SYSTEM AND METHOD FOR OPTIMIZING THE EFFICIENCY OF PHOTO-POLYMERIZATION

(71) Applicant: Excelsior Nanotech Corporation, Tempe, AZ (US)

(72) Inventors: Cody Youngbull, Tempe, AZ (US); Lixin Zheng, Kirkland, WA (US)

(73) Assignee: Excelsior Nanotech Corporation, Bellevue, WA (US)

( * ) Notice: Subject to any disclaimer, the term of this patent is extended or adjusted under 35 U.S.C. 154(b) by 0 days.

(21) Appl. No.: 14/600,060

(22) Filed: Jan. 20, 2015

(65) Prior Publication Data
US 2015/0210783 A1    Jul. 30, 2015

Related U.S. Application Data

(60) Provisional application No. 61/933,301, filed on Jan. 29, 2014.

(51) Int. Cl.
| G01N 15/06 | (2006.01) |
| G01N 33/00 | (2006.01) |
| G01N 33/48 | (2006.01) |
| B03C 1/28 | (2006.01) |
| C12Q 1/68 | (2006.01) |
| C08F 2/50 | (2006.01) |
| G01N 33/44 | (2006.01) |
| B03C 1/032 | (2006.01) |

(52) U.S. Cl.
CPC ............... *C08F 2/50* (2013.01); *G01N 33/442* (2013.01)

(58) Field of Classification Search
CPC ....... G01N 15/06; G01N 33/00; G01N 33/48; B03C 1/29; B03C 1/032; C12Q 1/68
USPC .............. 422/50, 400, 68.1, 82.05, 129, 131, 422/186, 502, 503, 94, 603; 436/174, 164; 977/700, 773
See application file for complete search history.

(56) References Cited

U.S. PATENT DOCUMENTS

| 5,712,322 | A | 1/1998 | Ghosh | |
| 2005/0112671 | A1 | 5/2005 | Maletta | |
| 2007/0203312 | A1 | 8/2007 | Lee | |
| 2010/0255488 | A1 | 10/2010 | Kong | |
| 2010/0261263 | A1* | 10/2010 | Vo-Dinh et al. | ............ 435/287.1 |
| 2011/0033866 | A1 | 2/2011 | Fish | |
| 2011/0126889 | A1* | 6/2011 | Bourke et al. | ................ 136/253 |
| 2013/0251995 | A1 | 9/2013 | Hao | |
| 2013/0323685 | A1 | 12/2013 | Ostler et al. | |
| 2014/0148880 | A1* | 5/2014 | Deisseroth et al. | ........... 607/100 |
| 2014/0185284 | A1* | 7/2014 | Hsu et al. | ...................... 362/231 |
| 2014/0273255 | A1* | 9/2014 | Bisso et al. | ..................... 436/94 |
| 2014/0353218 | A1* | 12/2014 | Soukka | ......................... 209/214 |
| 2015/0210783 | A1 | 7/2015 | Youngbull | |

OTHER PUBLICATIONS

PCT/US2015/013388 International Search Report and the Written Opinion of the International Searching Authority dated Apr. 2, 2015.

* cited by examiner

*Primary Examiner* — Brian J Sines
(74) *Attorney, Agent, or Firm* — Glenn H. Lenzen; Dietze and Davis, P.C.

(57) ABSTRACT

An improved system for energy transfer photopolymerization which optimizes the transfer efficiency of energy from a low energy light source to a higher energy donor and then to a polymerization initiator for the polymerization of a monomer material. The energy transfer efficiency is optimized by introducing stably miscible surface treated upconverting nanocrystal donors into a monomer matrix for near infrared to blue and ultraviolet upconversion and resonantly coupling the energy stored in the donor to the initiator via Förster Resonance Energy Transfer (FRET).

22 Claims, 3 Drawing Sheets

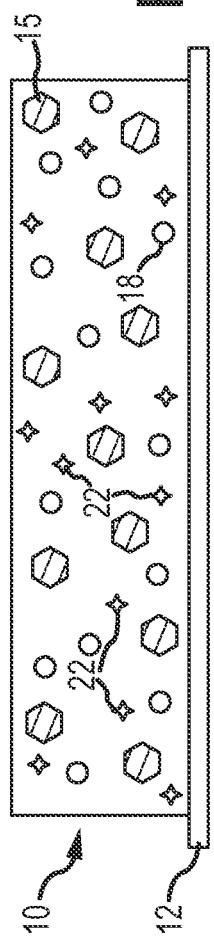
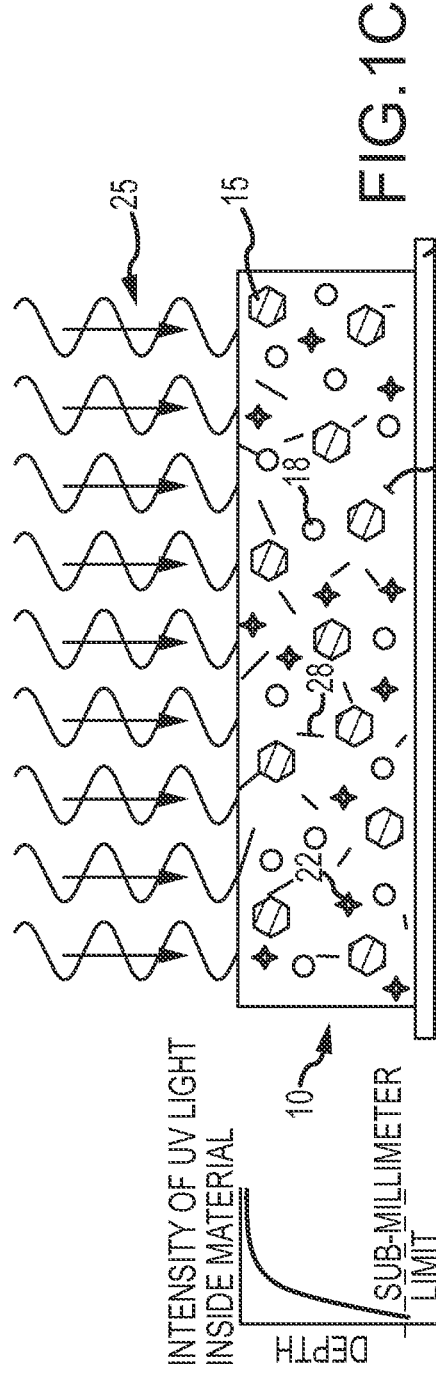
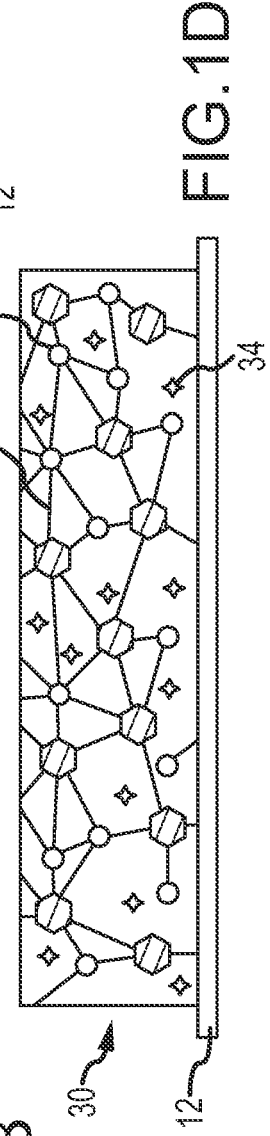

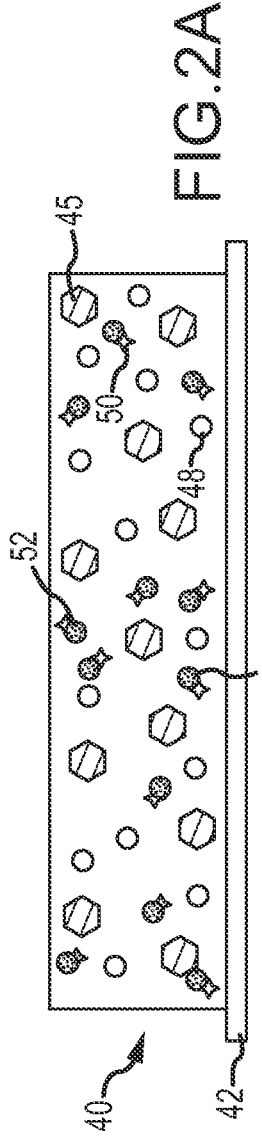
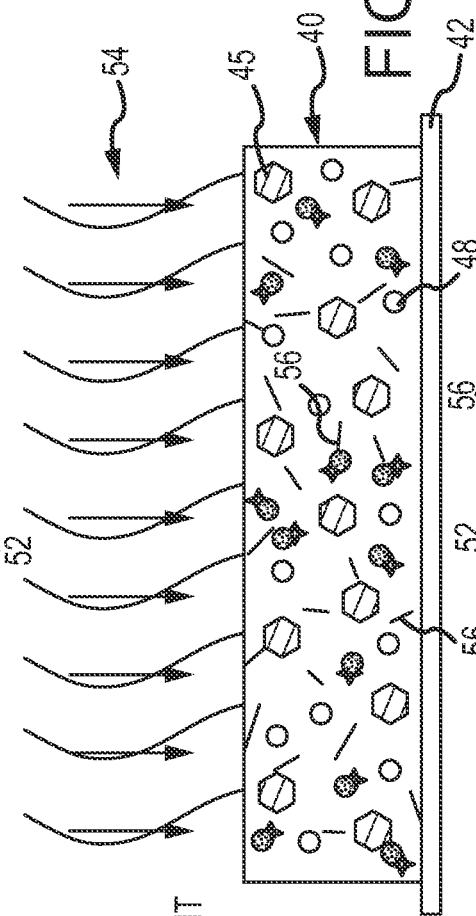
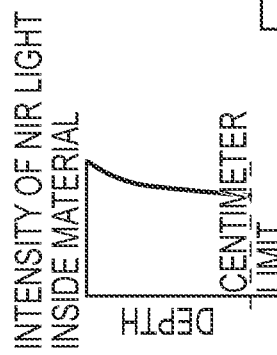
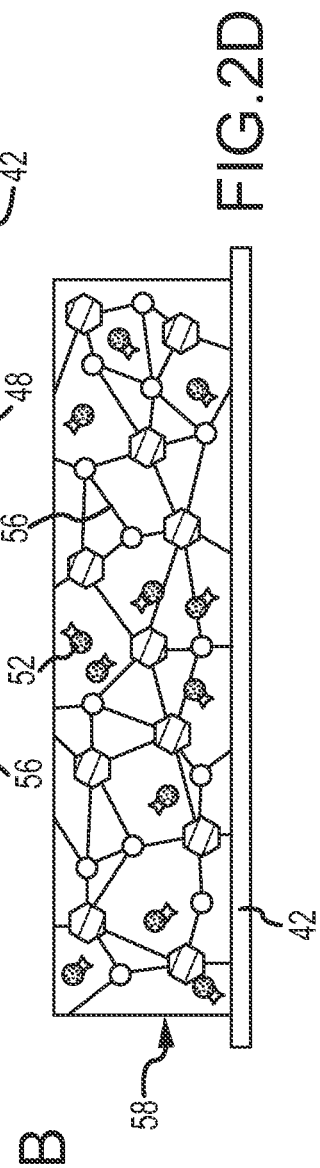

SYSTEM AND METHOD FOR OPTIMIZING THE EFFICIENCY OF PHOTO-POLYMERIZATION

PRIORITY TO RELATED PATENT APPLICATIONS

This application is a U.S. Patent Application which claims the benefit of U.S. Provisional Patent Application Ser. No. 61/933,301 filed Jan. 29, 2014, which is incorporated herein in its entirety by reference.

FIELD OF THE INVENTION

The present invention relates generally to photo-polymerization. More specifically, the present invention relates to systems and methods for optimizing the efficiency of energy transfer from upconverting nanoparticle to photoinitiator, which initiates photo-polymerization of monomer molecules.

BACKGROUND OF THE INVENTION

Energy in the form of electromagnetic radiation or light in frequency ranges extending from the radio frequency (rf) through visible light wavelengths to the x-ray wavelength range is used not only in the field of communications and lighting applications, but also in a wide range of industrial processes. Infra-red (IR) radiation, which is radiation found just beyond the red end of the visible spectrum and having a longer wavelength and lower frequency than visible light, may be used in medical applications such as therapeutic IR heat treatments and in communications systems.

Ultra-violet (UV) radiation, on the other hand, found just beyond the violet end of the visible light spectrum, has a shorter wavelength and higher frequency than IR radiation and is being used increasingly in various industrial, chemical and pharmaceutical applications. By way of example, UV radiation is capable of destroying microbiological organisms and is used for sterilization of medical instruments, toothbrushes and so forth. It also can be utilized to initiate certain photo-activated processes such as the cross-linking of existing polymers with one another in coating or adhesive applications (for example, the setting of epoxy resins in commonly used household and industrial glues) or in the polymerization of monomer molecules in a chemical reaction to form polymer chains or three-dimensional networks.

The wave/particle duality of the nature of light permits it to be characterized in terms of a wave having a wavelength and amplitude, analogous to a wave which may be observed on a body of water. Light may also be treated as a discrete particle of energy known as a photon characterized by its frequency times Planck's constant, h; accordingly, the higher the frequency of light, the higher the quantized energy carried by it.

As applications for electromagnetic energy of various frequencies and wavelengths evolved, it became desirable to convert light from one frequency range and energy level to another. Down conversion is the process of converting higher energy light to lower energy light. Conversely, upconversion is the process of converting lower energy light to higher energy light. Upconversion is typically a multi-photon absorption process where two or more photons are used to promote an excited electronic state in a host medium which, in turn, radiates at a wavelength of light that has a higher energy level than the energy of the incident light employed to initiate the process. Examples of up and down conversion systems and uses therefor are disclosed in U.S. Patent Application Publication No. US 2010/026123 published by Vo-Dinh et al., Oct. 14, 2010, now U.S. Pat. No. 8,389,958 B2, issued Mar. 5, 2013, and in U.S. Reissued Patent No. RE43, 944 E issued to Zhang et al., Jan. 29, 2013.

More specifically, the upconversion of lower energy near infrared (NIR) light to higher energy UV light has found application in the curing of certain polymers which are used in surgical, dental and prosthetic devices. See Alexander Stepuk, et al., *Use of NIR Light and Upconversion Phosphors in Light-Curable Polymers*, Jour. Of Dental materials, 28, pp. 304-311 (2012) and Uo, et al., *Preparation and Properties of Dental composite Resin Cured under Near Infrared Irradiation*, Jour. Of Photopolymer Science and Technology, 22(5): 551-554 (2009). Both articles discuss the use of additives or dopants to dental composite materials in conjunction with the application of NIR light energy to address the problems encountered in curing such materials using less penetrating UV energy. However, problems of efficiency and cost-effectiveness in practical commercial applications remain, as discussed in greater detail below.

Polymerization is the process of reacting monomer molecules together in a chemical reaction to form polymer chains or three-dimensional networks. Photo-induced polymerization or photopolymerization makes use of electromagnetic energy, i.e., photons, to initiate the polymerization reaction. Any photopolymerization process includes three basic molecular components: a sensitizer/donor, an initiator/acceptor, and a monomer (or pre-polymer). In some material systems, the initiator itself is photo-activatible and a sensitizer is not necessarily required.

The systems disclosed in the prior art using conventional energy transfer mechanism in the process of polymerization by NIR light require that the NIR light be first absorbed by a substrate matrix, typically a material comprised of nanocrystals of a selected composition. Photon-Phonon energy transfer effectively stores the NIR energy in the vibrational modes of the nanocrystals long enough for more NIR photons to arrive and excite the nanocrystals further, effectively integrating the NIR excitation to progressively higher levels. NIR to blue and UV upconversion is known to be a four- and five-photon integration process, respectively. The nanocrystals can emit the total stored energy as blue or UV light which can then be absorbed by the initiator in a process called re-absorption.

Normally, photopolymerization is induced by relatively high-frequency optical radiation such as ultraviolet (UV) and blue light as discussed above, because these wavelengths have sufficient energy to induce molecular changes in common initiators and sensitizers. The problem for UV and blue light is that the monomer penetration depth is wavelength dependent with higher frequencies being absorbed more rapidly. In other words, the UV energy has penetration depths of levels on the order of approximately one millimeter, as is shown in FIG. 1-2, Standard Method of Photopolymerization. Thick photo-cured systems of more than a few hundred microns are typically achieved in a layer-by-layer approach with reapplication of uncured materials at each step. Layer-by-layer deposition is time consuming and has the potential of introducing internal defects in the resultant solid.

Recently, a variety of different molecules and nanoparticles have been synthesized which are capable of converting low-frequency radiation to high-frequency radiation via the upconversion process. As discussed briefly above, upconversion obeys energy conservation because more photons of lower energy are converted to fewer photons of higher energy. In general, the process can be referred to as multi-photon conversion, and different molecules and nanoparticles achieve the effect by totally different linear and non-linear optical means. Upconverting materials suggest a mechanism of utilizing lower energy light, including near infra-red light to induce photopolymerization without modifying industry accepted initiator/monomer systems. Using lower energy light to initiate polymerization is attractive because of the availability of lower-cost light sources and the deeper penetration depth, in particular when using NIR light as opposed to potentially dangerous and eye-damaging UV light.

One increasingly popular approach to upconversion is to use inorganic nanoparticles, or nanocrystals, doped with Rare Earth elements. Sodium Yttrium Fluoride (NaYF4) nanocrystals doped with various other Rare Earth elements such as Erbium, Europium, Ytterbium and Thulium have recently been identified by numerous groups to be capable of converting NIR to red (Europium), green (Ytterbium), blue and UV (Thulium). NaYF4 nanocrystals have the added benefits of being intrinsically colorless and have been shown to be non-toxic in animals and single cells. However, NaYF4 and other potentially useful nanocrystals are not directly miscible with many industry standard monomer systems.

Accordingly, a need exists for a system and method for improving the efficiency of energy transfer-initiated photopolymerization using lower energy light sources and permitting deeper, single operation polymerization processes in commercial applications via the use of stably miscible nanocrystals in a monomer matrix for improved, cost-effective quality control of the end product.

SUMMARY OF THE INVENTION

Accordingly, the present invention provides an improved system for energy transfer photopolymerization whereby efficiency of the transfer of energy from a low energy light source to higher energy donor and then to a polymerization initiator for polymerization of a monomer material is optimized.

In accordance with an embodiment, the efficiency of the energy transfer is optimized by providing surface treated upconverting nanocrystal donors for NIR to blue and UV upconversion which are stably miscible in a monomer matrix.

In yet another embodiment of the present invention the upconverting nanocrystal donors comprise sodium yttrium fluoride (NaYF4) nanocrystals doped with Rare Earth elements.

In another embodiment, the efficiency of the energy transfer from the upconverting nanocrystal donors to the initiator/acceptors is increased by resonantly coupling the energy stored in the donor to the initiator via Førster Resonance Energy Transfer (FRET).

In yet another embodiment, the upconverting initiator/acceptors are sensitive to blue light and UV radiation.

In still another embodiment of the present invention, the FRET efficiency is optimized by controlling the distance between the donor and the initiator/acceptor; controlling the spectral overlap of the donor emission spectrum and the acceptor absorption spectrum; and by controlling the relative orientation of the donor emission dipole moment and the acceptor absorption dipole moment.

These and other objects of the present invention will be apparent from the accompanying figures, description of the invention and supplemental supporting materials provided herein.

BRIEF DESCRIPTION OF THE FIGURES

FIG. 1A is a side elevation view of a monomer-oligomer matrix prepared for a standard photopolymerizaton process;

FIG. 1B illustrates graphically the decrease of the intensity of ultraviolet (UV) light inside a material as a function of depth;

FIGS. 1C and 1D are side elevation sectional views of a monomer-oligomer matrix illustrating the standard method of photopolymerization utilizing ultraviolet (UV) light;

FIG. 2A is a side elevation view of a monomer-oligomer matrix prepared for an upconverting method of photopolymerization using near infrared (NIR) light;

FIG. 2B illustrates graphically the degree of penetration of near infrared (NIR) light into a material as a function of depth;

FIGS. 2C and 2D are side elevation sectional views of a monomer-oligomer matrix illustrating an upconverting method of photopolymerization utilizing near infrared (NIR) light.

DESCRIPTION OF THE INVENTION

Figure 3:
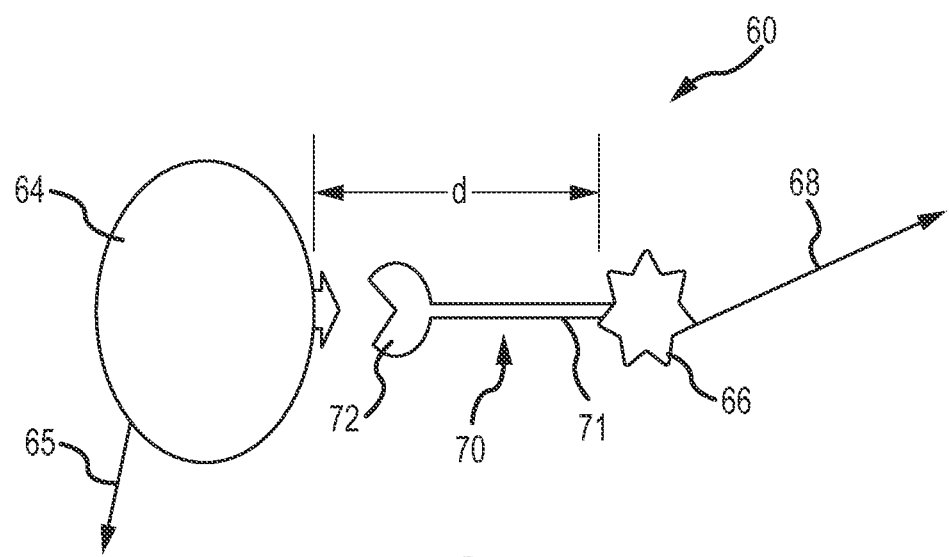
FIG. 3 is a side view of an energy transfer photopolymerization system of the present invention showing the elements thereof in greater detail.

It should be noted that the present description is by way of illustration only, and that the concepts and examples presented herein are not limited to use or application of any single system for energy transfer photopolymerization. Hence, while the details of the photopolymerization system described herein are for the convenience of illustration and explanation with respect to the exemplary embodiments, the principles disclosed may be applied to other types of photopolymerization systems without departing from the scope of the present invention.

By way of further background, polymers are large molecules composed of repeated sub-units called monomers. Natural examples include, cotton, wool, amber, silk, starch, rubber and DNA. Common synthetic polymers include synthetic rubber, phenol formaldehyde resin (or Bakelite), neoprene, nylon, polyvinyl chloride (PVC or vinyl), polystyrene, polyethylene, polypropylene, polyacrylonitrile, polyimide, PVB, and silicone. The list is immense. Each of these named polymers encompasses a class of materials that can have wide ranging properties.

Many of the most useful industrial polymers are processed in a liquid state before they are "cured". Curing is a term that refers to the hardening of a polymer material by cross-linking of polymer chains, a process which may be affected via the addition of chemicals, exposure to ultraviolet and/or electron beam radiation, or heat. A term known in the vernacular with respect to the curing of rubber is the curing process known as "vulcanization". Any chemical that is mixed into a polymer (usually while still in its liquid state) to modify its properties or its processability is considered an "additive". Some additives do nothing more than modify a polymer's color. Some completely change the hardness and texture of the cured polymer. The present invention is directed to new and improved additive compositions and photopolymerization methodologies which optimize the energy transfer efficiency therein, and it is to those subjects which the reader's attention is now directed.

Referring now to FIGS. 1A through 1D, an optically-curable monomer-oligomer matrix 10 illustrating the standard method of photopolymerization utilizing blue or potentially dangerous ultraviolet (UV) light is shown in cross sectional detail. The matrix is supported by a substrate 12 and includes a plurality of oligomers 15, monomers 18 and photoinitiators 22 disbursed throughout the system, each being of a preselected composition suitable for the intended final application for the polymerized system.

As shown in greater detail in FIG. 1C, the uncured matrix 10 is exposed to either blue or UV radiation 25 to initiate the polymerization process. The UV radiation excites the photoinitiators to higher energy levels sufficient to induce polymerization. However, as illustrated graphically in FIG. 1B, the absorption of the incident blue or UV radiation in the matrix material is high, being inversely proportional to its wavelength, which results in a rapid decline in the degree of polymerization which actually occurs with the depth from the matrix surface. Hence, the distribution of polymer chains throughout the matrix is non-uniform, being more concentrated toward the upper surface of the matrix and exhibiting a rapid decline in degree of polymerization with depth. This is illustrated graphically in FIG. 1C by the decreasing length of the polymer chains 28 as one progresses from the top toward the bottom of the matrix. The final product is a cured matrix 30 shown in FIG. 1D which comprises the polymerized oligomer-monomer structure 32 and consumed photoinitiators 34.

FIGS. 2A through 2D illustrate a preferred system and method of energy transfer photopolymerization incorporating the unique and novel subject matter of the instant invention. An optically-curable monomer-oligomer matrix 40 illustrating an upconverting method of photopolymerization using eye-safe near infrared (NIR) light is shown in cross sectional detail. The matrix 40 is supported by a substrate 42 and includes a plurality of nanocrystals in the form of oligomers 45, monomers 48 and photoinitiators 50 disbursed throughout the system, each being of a preselected composition suitable for the intended final application for the polymerized system, as hereinabove described. The monomers are polymerizable, co-polymerizable and/or preferably photo-polymerizable, and by way of illustration and not of limitation, may comprise monomer acrylics. However, unlike the prior art systems as typified by the system of FIG. 1, in the unique and novel system of the present invention shown generally in the embodiments of FIG. 2, the monomer-oligomer matrix includes a plurality of supramolecular upconverting photoinitiators 52, the structure and properties of which will be described in greater detail below with respect to the supramolecular structure of the unique nanocrystal illustrated in FIG. 3.

As shown in FIG. 2C, the uncured matrix 40 is exposed to eye-safe NIR light 54 to initiate the polymerization process. The NIR light, being of longer wavelength than the UV radiation discussed above with respect to the photopolymerization process illustrated in FIG. 1, has a much greater degree of penetration into the matrix 40 (FIG. 2B). Accordingly, a significantly greater degree of uniformity of polymerization throughout the entire thickness of the matrix material is realized, as shown graphically in FIG. 2C by the relatively uniform distribution of polymer chains 56 throughout the matrix. The degree and depth of polymerization in the cured matrix 58 shown in FIG. 2-3 are achieved with significantly enhanced efficiency in accordance with the novel processes and material compositions of the embodiments of the instant invention by converting the low energy NIR radiation into high energy visible blue and UV radiation within and throughout the matrix itself. However, internal absorption of the blue and UV radiation (absorption of light generated within the material itself) interferes with the efficiency of this process. This problem is overcome via the application of supramolecular chemistry principles to obtain the unique nanocrystal structures and associated properties of the various elements of the system of the present invention.

The supramolecular structure of an exemplary nanocrystal of the present invention is illustrated in FIG. 3. Supramolecular chemistry refers to the domain of chemistry beyond that of molecules and focuses on the chemical systems made up of a discrete number of assembled subunits, functional groups and moieties. In organic chemistry, functional groups are specific groups of atoms or bonds within molecules that are responsible for the characteristic chemical reactions of those molecules. The term "moiety" is often used interchangeably with "functional group"; however, the preferred definition is that a moiety is part of a molecule that may include either whole functional groups or parts of functional groups as substructures. For the purposes of this invention, the above-referenced definitions will apply to those terms as used herein. It is via the selective incorporation of multifunctional nanocrystalline structures and terminated moieties possessing desired physical properties specific to the applications of the polymers created by the methodologies disclosed herein that the unique and energy efficient processes and resultant materials are achieved.

Referring now to FIG. 3, elements of the system for energy transfer photopolymerization are shown in greater detail. A supramolecular nanoparticle structure is shown generally at 60 and includes an upconverting nanoparticle/nanocrystal energy donor 64, a photoinitiator or energy acceptor 66 located a preselected intramolecular distance, d, from the donor, and means 70 for linking the donor 64 to the acceptor, the linking means being structured and arranged to establish and maintain the intramolecular distance d in a preferred range of approximately 1 to approximately 20 nanometers so as to optimize the energy transfer there between. The energy donor is adapted to release energy stored therein in response to exposure to energy having a first preselected wavelength (represented graphically by arrow 65), and the acceptor is structured and arranged to release energy having a second, different preselected wavelength (represented graphically by arrow 68) in response to the resonant transfer of energy from the donor to the acceptor. Unlike the energy transfer mechanism described above with respect to the method of photopolymerization wherein upconverted photons propagate in random directions throughout the material matrix, the system and method of the present invention optimizes the efficiency of the energy transfer from the upconverting nanocrystal donors to the initiator/acceptors by resonantly coupling the energy stored in the donor to the initiator via Förster Resonance Energy Transfer (FRET). FRET is fundamentally non-radiative and, as such, the upconverted (visible blue or UV) photon is never actually produced. Rather, its energy is resonantly transferred to a light absorbing moiety (in this case the photoinitator) in the supramolecular structure comprised of the nanocrystal-ligand-photoinitiator. This is critically different from the systems and methods of the prior art wherein the upconverted photon is produced in reality and then propagated toward a photoinitiator. In the later, the real photon is absorbed by the intervening matrix material, and only a small fraction of the time the photoinitiator actually absorbs the real photon. Hence, the process is extremely inefficient.

A main concern associated with prior art systems is the lack of compatibility or miscibility of the supramolecular upconverting system with existing polymer systems. Accordingly, in accordance with an embodiment of the present invention, the multi-functional nanocrystalline polymer additive donors described herein are inorganic rare earth elements which are surface-treated or ligand-coated/passivated, as that term is used in the art, to make them miscible (dissolved or stably and uniformly suspended) in existing polymer systems. The rare earth elements are selected from the group consisting of Erbium (Er), Ytterbium (Yb), Thulium (Tm) and Europium (Eu). Preferably, each of the donors comprises a submicron nanoparticle, the nanoparticle being selected from the group of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, $SiO_2$, and alloys and layers thereof.

In addition to selectively controlling and maintaining the intramolecular distance or spacing d between the donor and the acceptor, the resonant energy transfer efficiency may be further optimized by judicious selection and matching of the respective energy emission and energy absorption spectra of the donor and the acceptor and, to the extent possible, the relative orientations of the donor with respect to the acceptor. A donor will have an energy emission spectrum of a known spectral range, and an acceptor will have an absorption spectrum of a known spectral range. By selecting the donor and the acceptor such that the energy emission spectrum and the energy absorption spectrum bandwidths at least partially overlap, the efficiency of the energy transfer between the two elements, and therefore the efficiency of the NIR photo-polymerization photoinitiation process will be optimized.

The acceptor may be selected from the group of compounds comprising photo-acid generators or free radical generators. In a preferred embodiment, the acceptor may be selected from the group consisting of Azobisisobutyronitrile (AIBN), Benzoyl peroxide, Camphorquinone, Trimethylbenzoyl-diphenylphosphine oxide, Phenyl propanedione, Ethyl dimethylamino benzoate, Dihydroxyethyl-para-toluidine, dimethylaminoethyl methacrylate, Irgacure, Irgacure PAG, or CGI.

Referring again to FIG. 3, the linking means preferably comprises an organic or an inorganic molecule 71 operatively connected to both the donor and the acceptor. By way of example and not of limitation, the linker may be in the form of an organic molecule such as an alkyl chain, a hydrophobic or hydrophilic oligomer, preferably a sub 20 nm molecule. The linking means 70 further includes a terminated moiety 72 structured and arranged to bind the linking means to the donor 64, the terminated moiety being selected from the group of terminated moieties consisting of amine-terminated, hydroxyl-terminated, phosphoric-terminated, aldehyde-terminated, pyridine-terminated, and carboxylic acid-terminated moieties.

In view of the foregoing, it can be seen that the efficiency of near-infrared photo initiation of photo polymerization in a photo polymerization system may be optimized by careful processing of the following steps and modifying the system components in response to the effects of the individual contributing parameters upon overall photoinitiation efficiency:

a) synthesizing samples of the linking means having lengths such that the distance between the donor and the acceptor is in a range of zero to 20 nanometers;

b) synthesizing samples of the photo polymerization system in which the linking means is operatively connected to the acceptor at different locations thereon whereby the relative orientation of the acceptor with respect to the donor is varied;

c) synthesizing samples of the donor and the acceptor to maximize the overlap of the donor energy emission and the acceptor energy absorption spectra;

d) mixing the samples of the photo polymerization system into a monomer material in concentrations ranging from approximately 0.01 percent by weight to approximately 5 percent by weight;

e) exposing the monomer-photo polymerization system mixture to a known dosage of near infrared radiation;

f) measuring the amount of monomer which is polymerized; and g) optionally repeating steps a) through f) to optimize: 1. the distance between the donor and the acceptor, 2. the orientation there between, 3. the overlap of the donor energy emission and the acceptor energy absorption spectra, and 4. the concentration of the photo polymerization system into a monomer material, whereby the efficiency of the near-infrared photo initiation of the photo polymerization of the monomer is maximized.

Changes may be made in the above methods, devices and structures without departing from the scope hereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, device and structure, which, as a matter of language, might be said to fall there between.

What is claimed is:

1. A resonantly-coupled, non-radiative photo polymerization energy transfer system for curing an optically curable monomer-oligomer matrix, the system comprising:
    at least one supramolecular upconverting nanoparticle structure surface treated with a ligand coating, whereby the nanoparticle structure is uniformly soluble and stably miscible in the matrix, the nanoparticle structure including:
        at least one upconverting nanoparticle energy donor adapted to release energy having a first preselected wavelength in response to exposure to energy having a wavelength falling in the near infrared or infrared spectrum;
        at least one photo-initiating, energy absorbing acceptor moiety located at a preselected intramolecular distance d from the at least one energy donor, the photo-initiating moiety being adapted to receive the energy released by the at least one energy donor;
        a molecule adapted to link the at least one energy donor to the at least one acceptor moiety, the linking molecule being structured and arranged to establish and maintain the preselected intramolecular distance between the at least one energy donor and the at least one acceptor moiety; and
        a terminated moiety structured and arranged to bind the linking molecule to the energy donor and to control the relative orientation of the energy donor with respect to the acceptor moiety;
    whereby the relative orientation of the energy donor with respect to the acceptor moiety and the preselected intramolecular distance d cooperate with one another to optimize the resonantly-coupled, non-radiative energy transfer from the energy donor to the acceptor moiety.

2. The system of claim 1 wherein the at least one donor includes at least one rare earth element.

3. The system of claim 2 wherein the rare earth element is selected from the group consisting of Erbium (Er), Ytterbium (Yb), Thulium (Tm) and Europium (Eu).

4. The system of claim 2 wherein the donor comprises a submicron nanoparticle, the nanoparticle being selected from the group of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, $SiO_2$, and alloys and layers thereof.

5. The system of claim 1 wherein the molecule linking the at least one energy donor to the at least one acceptor moiety comprises an organic molecule.

6. The system of claim 5 wherein the organic molecule comprises an alkyl chain.

7. The system of claim 1 wherein the molecule linking the at least one energy donor to the at least one acceptor moiety comprises an inorganic molecule.

8. The system of claim 5 wherein the linking molecule comprises a sub 20 nm molecule.

9. The system of claim 1 wherein the linking molecule comprises a sub 20 nm molecule.

10. The system of claim 8 wherein the linking means comprises a hydrophobic or hydrophilic oligomer.

11. The system of claim 1 wherein the terminated moiety is selected from the group of terminated moieties consisting of amine-terminated, hydroxyl-terminated, phosphoric-terminated, aldehyde-terminated, pyridine-terminated, and carboxylic acid-terminated moieties.

12. The system of claim 1 wherein the preselected intramolecular distance d is in the range of approximately 1 nm to approximately 20 nm.

13. The system of claim 1 wherein the at least one monomer-oligomer matrix is co-polymerizable.

14. The system of claim 1 wherein the at least one monomer-oligomer matrix comprises a monomer acrylic system.

15. The system of claim 1 wherein the acceptor moiety is a photo-acid generator.

16. The system of claim 1 wherein the acceptor moiety is a free radical generator.

17. The system of claim 1 wherein the acceptor moiety is selected from the group consisting of Azobisisobutyronitrile (AIBN), Benzoyl peroxide, Camphorquinone, Trimethylbenzoyl-diphenylphosphine oxide, Phenyl propanedione, Ethyl dimethylamino benzoate, Dihydroxyethyl-para-toluidine, dimethylaminoethyl methacrylate, Irgacure, Irgacure PAG, or CGI.

18. The system of claim 1 wherein the at least one acceptor moiety is structured and arranged to release energy having a second preselected wavelength in response to the resonant transfer of energy from the donor to the acceptor moiety.

19. The system of claim 18 wherein the donor includes an energy emission spectrum of a known spectral range.

20. The system of claim 19 wherein the acceptor moiety includes an absorption spectrum of a known spectral range.

21. The system of claim 20 wherein the donor and the acceptor are selected such that the energy emission spectrum and the absorption spectrum bandwidths at least partially overlap to optimize the efficiency of the near infrared photo initiation.

22. A method for optimizing the efficiency of near-infrared photo initiation of photo polymerization in an optically-curable monomer-oligomer matrix of a photo polymerization system, the system including a nanoparticle energy donor adapted to generate and store energy internally therein in response to exposure to energy having a first preselected wavelength, the donor having an energy emission spectrum of a known spectral range; a photoinitiator acceptor located at a preselected molecular distance from and in a relative orientation with respect to the donor and adapted to resonantly receive energy stored internally by the donor, the acceptor having an absorption spectrum of a known spectral range; means for resonantly transferring the energy internally stored in the donor to the acceptor without producing upconverting photons; and means for operatively linking the donor and the acceptor, the method comprising:
  a) synthesizing samples of the linking means having lengths such that the distance between the donor and the acceptor is in a range of zero to 20 nanometers;
  b) synthesizing samples of the photo polymerization system in which the linking means is operatively connected to the acceptor at different locations thereon whereby the relative orientation of the acceptor with respect to the donor is varied;
  c) synthesizing samples of the donor and the acceptor to maximize the overlap of the donor energy emission and the acceptor energy absorption spectra;
  d) surface treating the photopolymerization system with a ligand coating, whereby the photopolymerization system is uniformly soluble and stably miscible in the monomer-oligomer matrix;
  e) mixing the samples of the photo polymerization system into the monomer-oligomer matrix material in concentrations ranging from approximately 0.01 percent by weight to approximately 5 percent by weight;
  f) exposing the monomer-photo polymerization system mixture to a known dosage of near infrared radiation;
  g) measuring the amount of monomer which is polymerized; and
  h) optionally repeating steps a) through f) to optimize: 1. the distance between the donor and the acceptor, 2. the orientation there between, 3. the overlap of the donor energy emission and the acceptor energy absorption spectra, and 4. the concentration of the photo polymerization system into a monomer-oligomer matrix material, whereby the efficiency of the near-infrared photo initiation of the photo polymerization of the monomer-oligomer matrix material is maximized.

\* \* \* \* \*